(12) United States Patent
Lipowsky et al.

(10) Patent No.: US 7,745,658 B2
(45) Date of Patent: Jun. 29, 2010

(54) PROCESS FOR PREPARING TERTIARY ALKYL ESTERS OF (METH)ACRYLIC ACID HAVING AT LEAST 4 CARBON ATOMS IN THE ALKYL RADICAL

(75) Inventors: Gunter Lipowsky, Schriesheim (DE); Joachim Wulff-Doering, Frankenthal (DE); Peter Zurowski, Landau (DE); Juergen Strasser, Freinsheim (DE)

(73) Assignee: BASF SE, Ludwigshafen (DE)

( * ) Notice: Subject to any disclaimer, the term of this patent is extended or adjusted under 35 U.S.C. 154(b) by 2 days.

(21) Appl. No.: 12/168,342

(22) Filed: Jul. 7, 2008

(65) Prior Publication Data

US 2009/0023947 A1    Jan. 22, 2009

(30) Foreign Application Priority Data

Jul. 19, 2007  (EP)  .................. 07112756

(51) Int. Cl.
    *C07C 69/52*    (2006.01)
(52) U.S. Cl. ..................................... 560/205
(58) Field of Classification Search ........ None
    See application file for complete search history.

(56) References Cited

U.S. PATENT DOCUMENTS 5,322,960 A * 6/1994 Sakamoto et al. ........... 560/205
2003/0181754 A1* 9/2003 Kroker et al. ............... 560/241

* cited by examiner

*Primary Examiner*—Paul A Zucker
(74) *Attorney, Agent, or Firm*—Oblon, Spivak, McClelland, Maier & Neustadt, L.L.P.

(57) ABSTRACT

The present invention relates to a process for preparing tertiary alkyl esters of (meth)acrylic acid having at least 4 carbon atoms in the alkyl radical. The process includes reacting (meth)acrylic acid with at least one olefin of formula (I) in homogeneous phase in the presence of an acidic catalyst in a reactor, discharging the resulting reaction mixture from the reactor, separating the discharged reaction mixture into a first mixture which contains the catalyst and a second mixture which contains the tertiary alkyl ester of (meth)acrylic acid having at least 4 carbon atoms in the alkyl radical, and removing the tertiary alkyl ester of (meth)acrylic acid having at least 4 carbon atoms in the alkyl radical from the second mixture in the presence of compound S, which comprises at least one N-oxyl group and is added as a stabilizer.

20 Claims, No Drawings

PROCESS FOR PREPARING TERTIARY ALKYL ESTERS OF (METH)ACRYLIC ACID HAVING AT LEAST 4 CARBON ATOMS IN THE ALKYL RADICAL

FIELD OF THE INVENTION

The present invention relates to a novel process for preparing tertiary alkyl esters of (meth)acrylic acid having at least 4 carbon atoms in the alkyl radical

STATE OF THE ART

In the context of the present invention, the expression "(meth)acrylic acid" is understood to mean the abbreviation of "acrylic acid or methacrylic acid" and also "acrylic acid and methacrylic acid". Accordingly, the expression "(meth)acrylic ester" is understood to mean the abbreviation of "acrylic ester or methacrylic ester" and also "acrylic ester and methacrylic ester".

A process for preparing tertiary alkyl esters of (meth)acrylic acid having from 4 to 8 carbon atoms in the alkyl radical, which comprises the process steps of:

(1) reacting (meth)acrylic acid with at least one olefin of the general formula:

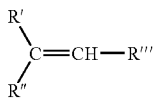

in which R' and R" may be the same or different and are each methyl or ethyl, and R'" is hydrogen, methyl or ethyl; in homogeneous phase in the presence of an acidic catalyst in a reactor, (2) discharging the resulting reaction mixture (1) from the reactor, (3) separating the discharged reaction mixture (2) into a mixture (3.1) which comprises the catalyst and a mixture (3.2) which comprises the tertiary alkyl ester of (meth)acrylic acid having from 4 to 8 carbon atoms in the alkyl radical, and (4) removing the tertiary alkyl ester of (meth)acrylic acid having from 4 to 8 carbon atoms in the alkyl radical from the mixture (3.2), is known from German patent application DE 100 36 959 A1. What is proposed herein is to perform the reaction in process step (1), in the presence of stabilizers such as hydroquinone, hydroquinone monomethyl ether, p-benzoquinone, p-nitrosophenol (PNP), phenothiazine (PTZ), 4-hydroxy-2,2,6,6-tetramethyl-1-oxylpiperidine (OH-Tempo) and/or methylene blue.

However, it has been found that OH-Tempo, under the given reaction conditions of the acidic catalyst, especially of sulfuric acid, is decomposed rapidly. The decomposition is accelerated further by the presence of PTZ. OH-Tempo is therefore useful—if at all—only to a very restricted degree as a stabilizer in the reaction in process step (1). The most effective stabilizer here is found to be PTZ, especially in combination with hydroquinone monomethyl ether.

In the known processes, stabilizers have to be used in the workup in process steps (3) and (4). While the mixture (3.1) in process step (3) still comprises the stabilizer used in the reaction, the mixture (3.2) removed is substantially or completely stabilizer-free and therefore has to be stabilized again for process step (4).

According to DE 100 36 959 A1, the stabilizers used are mixtures of PTZ and PNP. PNP, however, is known to have disadvantages. For instance, it is self-igniting, toxic, explosive and comparatively expensive. However, it is not possible to dispense with it entirely because the stabilizing action of PTZ in the workup leaves something to be desired, such that the risk of polymerization in the distillation columns and of fouling in the column bottom exists.

Problem

It is an object of the present invention to provide a novel process for preparing tertiary alkyl esters of (meth)acrylic acid having at least 4 carbon atoms in the alkyl radical, which comprises the process steps of:

(1) reacting (meth)acrylic acid with at least one olefin of the general formula I:

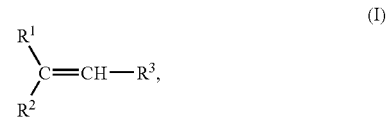

in which $R^1$ and $R^2$ may be the same or different and are each an alkyl radical, and $R^3$ is a hydrogen atom, an alkyl radical, a cycloalkyl radical, an aryl radical, an alkylcycloalkyl radical which is bonded to the olefinically unsaturated carbon atom via an aliphatic or cycloaliphatic carbon atom, an alkylaryl radical which is bonded to the olefinically unsaturated carbon atom via an aliphatic or aromatic carbon atom, a cycloalkylaryl radical which is bonded to the olefinically unsaturated carbon atom via a cycloaliphatic or aromatic carbon atom, or an alkylcycloalkylaryl radical which is bonded to the olefinically unsaturated carbon atom via an aliphatic, cycloaliphatic or aromatic carbon atom;

in homogeneous phase in the presence of an acidic catalyst in a reactor, (2) discharging the resulting reaction mixture (1) from the reactor, (3) separating the discharged reaction mixture (2) into a mixture (3.1) which comprises the catalyst and a mixture (3.2) which comprises the tertiary alkyl ester of (meth)acrylic acid having at least 4 carbon atoms in the alkyl radical, and (4) removing the tertiary alkyl ester of (meth)acrylic acid having at least 4 carbon atoms in the alkyl radical from the mixture (3.2), and which no longer has the disadvantages of the prior art. In particular, the novel process should permit, without the use of PNP, the removal of the tertiary alkyl esters of (meth)acrylic acid from the remaining constituents of the reaction mixture and their isolation in particularly high purity and in particularly high yield, without there being any polymerization, fouling and/or redissociation.

Inventive Solution

Accordingly, the novel process has been found for preparing tertiary alkyl esters of (meth)acrylic acid having at least 4 carbon atoms in the alkyl radical, comprising the steps of:

(1) reacting (meth)acrylic acid with at least one olefin of the general formula I:

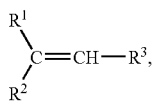

in which R¹ and R² may be the same or different and are each an alkyl radical, and R³ is a hydrogen atom, an alkyl radical, a cycloalkyl radical, an aryl radical, an alkylcycloalkyl radical which is bonded to the olefinically unsaturated carbon atom via an aliphatic or cycloaliphatic carbon atom, an alkylaryl radical which is bonded to the olefinically unsaturated carbon atom via an aliphatic or aromatic carbon atom, a cycloalkylaryl radical which is bonded to the olefinically unsaturated carbon atom via a cycloaliphatic or aromatic carbon atom, or an alkylcycloalkylaryl radical which is bonded to the olefinically unsaturated carbon atom via an aliphatic, cycloaliphatic or aromatic carbon atom;

in homogeneous phase in the presence of an acidic catalyst in a reactor, (2) discharging the resulting reaction mixture (1) from the reactor, (3) separating the discharged reaction mixture (2) into a mixture (3.1) which comprises the catalyst and a mixture (3.2) which comprises the tertiary alkyl ester of (meth)acrylic acid having at least 4 carbon atoms in the alkyl radical, and (4) removing the tertiary alkyl ester of (meth)acrylic acid having at least 4 carbon atoms in the alkyl radical from the mixture (3.2), and in which, (5) in process step (4), at least one compound S which comprises at least one N-oxyl group is added as a stabilizer.

For the sake of brevity, the novel process for preparing tertiary alkyl esters of (meth)acrylic acid having at least 4 carbon atoms in the alkyl radical will be referred to hereinafter as "process according to the invention".

Advantages of the Invention

With regard to the prior art, it was surprising and unforeseeable for the person skilled in the art that the problem addressed by the present invention could be solved with the aid of the process according to the invention.

In particular, it was surprising that the novel process permitted, without the use of PNP, removal of the tertiary alkyl ester of (meth)acrylic acid having at least 4 carbon atoms in the alkyl radical from the remaining constituents of the reaction mixture and its isolation in particularly high purity and in particularly high yield, without there being any polymerization, fouling and/or redissociation.

Surprisingly, it was also possible to achieve an additional stabilizing effect in the reaction in process step (1) if the products which had been removed in process step (4) from the tertiary alkyl ester of (meth)acrylic acid having at least 4 carbon atoms in the alkyl radical were recycled back into the reactor. This additional stabilizing effect brought about a further improvement in the yield.

DETAILED DESCRIPTION OF THE INVENTION

The process according to the invention serves to prepare tertiary alkyl esters of (meth)acrylic acid having at least 4 carbon atoms, especially from 4 to 8 carbon atoms, in the alkyl radical. For the sake of brevity, the tertiary alkyl esters of (meth)acrylic acid having at least 4 carbon atoms in the alkyl radical are referred to hereinafter as "target esters".

Examples of suitable target esters are tert-butyl acrylate and methacrylate, 2-methylbut-2-yl acrylate and methacrylate, 2-methylpent-2-yl acrylate and methacrylate, 2-methylhex-2-yl acrylate and methacrylate, 2-methylhept-2-yl acrylate and methacrylate, 2-methyl-1-cyclohexylprop-2-yl acrylate and methacrylate, 2-methyl-1-phenylprop-2-yl acrylate and methacrylate, 2-methylbut-2-yl acrylate and methacrylate, 3-methylpent-3-yl acrylate and methacrylate, 3-methylhex-3-yl acrylate and methacrylate, 3-methylhept-3-yl acrylate and methacrylate, 3-methyloct-3-yl acrylate and methacrylate, 2-methyl-1-cyclohexylbut-2-yl acrylate and methacrylate, 2-methyl-1-phenylbut-2-yl acrylate and methacrylate, 3-methylpent-3-yl acrylate and methacrylate, 3-ethylpent-3-yl acrylate and methacrylate, 3-propylpent-3-yl acrylate and methacrylate, 1,1-diethylpent-1-yl acrylate and methacrylate, 1,1-diethylhex-1-yl acrylate and methacrylate, 3-(cyclohexylmethyl)pent-3-yl acrylate and methacrylate, and 3-(phenylmethyl)pent-3-yl acrylate and methacrylate, especially tert-butyl acrylic acid or tert-butyl acrylate (TBA) and tert-butyl methacrylic acid or tert-butyl methacrylate (TBMA).

The process according to the invention proceeds, in process step (1), from the reaction of (meth) acrylic acid with at least one, especially one olefin of the general formula I:

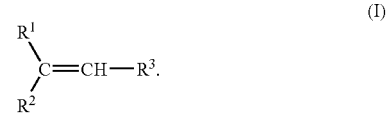

In the general formula I, R¹ and R² are the same or different and are each an alkyl radical, preferably having from 1 to 10, preferentially having from 1 to 6 and more preferably having from 1 to 4, carbon atoms, but especially meth-yl or ethyl.

In the general formula I R³ is a hydrogen atom;

an alkyl radical preferably having from 1 to 20, preferentially having from 1 to 10, and more preferably having from 1 to 4 carbon atoms, most preferably methyl, ethyl, propyl, isopropyl, n-butyl, isobutyl or tert-butyl, especially methyl or ethyl;

a cycloalkyl radical preferably having from 4 to 20, preferentially having from 5 to 16 and more preferably having from 6 to 10 carbon atoms, especially cyclohexane and a radical which derives from norbornane, bicyclo [2.2.2]octane, decalin, hydrindane or adamantane;

an aryl radical preferably having from 6 to 30, preferentially having from 6 to 20, and more preferably having from 6 to 14 carbon atoms, especially phenyl or a radical which derives from naphthalene or phenanthrene;

an alkylcycloalkyl radical which is bonded to the olefinically unsaturated carbon atom via an aliphatic or cycloaliphatic carbon atom, preferably having from 5 to 30, preferentially having from 7 to 20 and more preferably having from 7 to 10 carbon atoms, especially a radical which derives from methylcyclohexane, ethylcyclohexane, propylcyclohexane, n-butylcyclohexane, isobutylcyclohexane or tert-butylcyclohexane;

an alkylaryl radical which is bonded to the olefinically unsaturated carbon atom via an aliphatic or aromatic carbon atom, preferably having from 7 to 30, preferentially having from 7 to 20 and more preferably having from 7 to 10 carbon atoms, especially a radical which derives from toluene, xylene, ethylbenzene, propylbenzene, isopropylbenzene, n-butylbenzene, isobutylbenzene or tert-butylbenzene;

a cycloalkylaryl radical which is bonded to the olefinically unsaturated carbon atom via a cycloaliphatic or aromatic carbon atom, preferably having from 10 to 30, preferentially having from 10 to 20, and more preferably having from 10 to 16 carbon atoms, especially a radical which derives from cyclohexylbenzene;

an alkylcycloalkylaryl radical which is bonded to the olefinically unsaturated carbon atom via an aliphatic, cycloaliphatic or aromatic carbon atom, preferably having from 11 to 30, preferentially from 11 to 20 and more preferably from 11 to 16 carbon atoms, especially a radical which derives from 1-methyl-2-, -3- or -4-cyclohexylbenzene; but especially a hydrogen atom, or a methyl or ethyl group.

Examples of suitable olefins I are isobutene, trimethylene (2-methyl-2-butene), 2-methylpent-2-ene, 2-methylhex-2-ene, 2-methylhept-2-ene, 2-methyl-1-cyclohexylprop-1-ene, 2-methyl-1-phenylprop-1-ene, 2-methylbut-1-ene, 3-methylpent-2-ene, 3-methylhex-3-ene, 3-methylhept-3-ene, 3-methyloct-3-ene, 2-methyl-1-cyclohexylbut-1-ene, 2-methyl-1-phenylbut-1-ene, 2-ethylbut-1-ene, 3-ethylpent-2-ene, 3-ethylhex-3-ene, 3-ethylhept-3-ene, 3-ethyloct-3-ene, 2-ethyl-1-cyclohexylbut-1-ene and 2-ethyl-1-phenylbut-1-ene, especially isobutene.

The (meth)acrylic acid is reacted with the olefin I in homogeneous phase, especially in liquid homogeneous phase, preferably in the absence of a solvent. The reaction is effected in the presence of an acidic catalyst. The catalyst is preferably at least partly, preferably completely, soluble in the reaction mixture.

Examples of suitable catalysts are strong inorganic and organic acids, such as mineral acids or sulfonic acids. Examples of very suitable mineral acids are sulfuric acid, phosphoric acid and polyphosphoric acid, especially sulfuric acid. Examples of very suitable sulfonic acids are para-toluene-, benzene-, dodecylbenzene- and methanesulfonic acid.

The amount of the catalyst may vary widely and is guided by the requirements of the individual case. The amount is preferably from 1 to 10% by weight, preferably from 2 to 5% by weight, based on (meth)acrylic acid.

The olefin I may be used in gaseous and/or liquid form, especially in liquid form.

The (meth)acrylic acid used may comprise acetic acid, propionic acid and/or water in small amounts, preferably <2% by weight, especially <1% by weight, based on the (meth)acrylic acid. One example of a suitable (meth)acrylic acid is known from German patent DE 100 36 958 A1, column 3, paragraph [0018].

The reactants can be used in stoichiometric amounts. Preference is given to using one reactant in excess. This is preferably the (meth)acrylic acid. The excess may be up to 50 mol %.

The reaction conditions may vary widely and are guided by the requirements of the individual case. The reaction temperatures are preferably from 20 to 400° C. The reaction time is preferably from 1 to 6 hours. The pressure is not critical; it is possible to employ reduced pressure, elevated pressure or preferably ambient pressure or slightly elevated pressure, preferably 100 to 300 mbar (from $10^4$ to $3 \times 10^4$ Pa).

Preference is given to performing the reaction in the presence of at least one inhibitor which inhibits the polymerization of (meth)acrylic acid or of the target ester. Examples of suitable inhibitors are hydroquinone, hydroquinone monomethyl ether, para-benzoquinone, para-nitrosophenol (PNP), phenothiazine (PTZ), N-oxyl compounds such as 4-hydroxy-2,2,6,6-tetramethyl-1-oxylpiperidine (OH-Tempo) and methylene blue, preferably PTZ, especially PTZ and hydroquinone monomethyl ether.

In addition, it is also possible to use oxygen in the form of air or lean air as an inhibitor.

The concentration of the inhibitors may vary widely and is guided by the requirements of the individual case. They are preferably used in a concentration of from 200 to 10 000 ppm, based on the total weight of (meth)acrylic acid and olefin I.

The reaction can be performed continuously or batchwise in customary and known reactors. One example of a suitable reactor is known from German patent application DE 100 36 959 A1, column 3, paragraphs [0018] to [0020], and column 6, paragraph [0036], to column 7, paragraph [0042], in conjunction with the figure.

The composition of the resulting reaction mixture (1), which is discharged from the reactor in process step (2), can be adjusted through the composition of the starting materials, especially through the ratio of (meth)acrylic acid and olefin I, and can be varied widely. Examples of suitable compositions of discharged reaction mixtures (2) are known from German patent applications DE 100 36 959 A1, column 7, paragraph [0043] and DE 100 36 959 A1, column 4, paragraph [0022].

At the same time, any air and inert gases, such as butanes, present, and any excess olefin I present, can be discharged from the reactor separately from the reaction mixture (1). The olefin I can be condensed and sent back to the reaction.

In the further course of the process according to the invention, the discharged reaction mixture (2) is separated in process step (3), into a mixture (3.1) which comprises the catalyst, and a mixture (3.2) which comprises the target ester.

The reaction mixture (2) can be separated in a wide variety of different ways. For example, the mixture (3.1) can be removed by washing the reaction mixture (2) once or more than once with water and/or neutralizing the catalyst with an aqueous basic solution (for example, NaOH, KOH, aqueous sodium carbonate, sodium bicarbonate, potassium carbonate or potassium bicarbonate solution).

In particular, the separation into a mixture (3.1) and a mixture (3.2) is effected by distilling the reaction mixture (2), for example, in a distillation unit which comprises an evaporator, a column and a condenser. In this way, the mixture (3.2) is obtained as a top product which comprises essentially the target ester and small amounts of carboxylic acids and low-boiling constituents such as tert-butanol and diisoolefin. In addition, the mixture (3.1) is obtained as a bottom product which comprises the catalyst, the majority of unconverted (meth)acrylic acid and high-boiling constituents such as (meth)acrylate(co)polymers. The bottom product (3.1) can be recycled partly or completely into the reactor. Examples of a particularly advantageous process and a particularly advantageous apparatus for performing process step (3) are known from German patent application DE 100 36 98 A1, column 4, paragraph [0023], and column 5, paragraph [0029] up to line 30.

In the further course of the process according to the invention, the target ester is removed from the top product (3.2) in process step (4). This is preferably done by a two-stage distillation.

In this case, in the first distillation stage (4.1), the mixture (3.2) is separated into a low-boiling distillate (4.1.1) which comprises low boilers such as residual olefin I, especially isobutene, tert-butyl acetate, tert-butanol and diisoolefin, especially diisobutene, and a bottom product (4.1.2.) which comprises essentially the target ester and (meth)acrylic acid. An example of a suitable process for low boiler removal (4.1) is known from German patent application DE 100 36 98 A1, column 5, paragraph [0030], up to line 6, paragraph [0036] up to line 36.

The bottom product (4.1.2) is separated in the second distillation stage (4.2), i.e. in the purifying distillation, into a distillate (4.2.1) which consists essentially of the target ester and a bottom product (4.2.2). For this purpose, it is possible to use a customary and known distillation unit which comprises an evaporator, a column and a condenser. The bottom product (4.2.2) which comprises essentially (meth)acrylic acid is preferably recycled partly or completely into the reactor.

For the process according to the invention, it is essential that, in process step (4), at least one, especially one, compound S which comprises at least one, especially one, N-oxyl group is added as a stabilizer.

The N-oxyl group is preferably part of a heterocyclic, preferably aliphatic heterocyclic, ring. In particular, the aliphatic heterocyclic ring derives from a piperidine ring.

The N-oxyl group is preferably sterically hindered. The steric hindrance is preferably brought about by virtue of the carbon atoms in the alpha positions to the nitrogen atom of the N-oxyl group bearing in each case at least one, especially two, alkyl group(s). In particular, the alkyl groups are methyl groups.

The compound S preferably comprises at least one, especially one, 2,2,6,6-tetramethyl-1-oxylpiperidin-4-yl group.

The radical bonded to the 4 position of the 2,2,6,6-tetramethyl-1-oxylpiperidin-4-yl group may be a hydrogen atom, a halogen atom, preferably a fluorine, chlorine or bromine atom, a functional group, preferably a hydroxyl group, an amino group, a carboxylic acid group, a sulfonic acid group, a phosphonic acid group, a nitrile group, an isocyanate group or a nitro group, preferably a hydroxyl group or, an organic radical, preferably a monovalent, divalent or trivalent, preferably monovalent or divalent organic radical optionally comprising at least one heteroatom such as silicon, oxygen, sulfur or nitrogen, preferably having from 1 to 40 and more preferably from 1 to 30 carbon atoms, where the organic radical may be bonded to the 4 position via a carbon-carbon bond, an ether group, an ester group (—C(O)—O— radical or —O—C(O)— radical), an amino group, an amide group (—NHC(O)— radical or —C(O)—NH— radical) or a urethane group (—NH—C(O)—O— radical or —O—C(O)—NH— radical), for example an adipate radical or a sebacate radical.

In particular, it is a hydroxyl group. Accordingly, especially 4-hydroxy-2,2,6,6-tetramethyl-1-oxylpiperidine (OH-Tempo) is used as the compound S.

In the process according to the invention, the compound S can be added to the mixture (3.2) before the first distillation stage (4.1). This is preferably done by metering the compound S into the condenser of the distillation unit for the catalyst removal (process step 3). In this context, it is advantageous to meter in the compound S in the form of a dilute, preferably three percent, more preferably two percent and especially one percent, solution in the particular target ester which is to be isolated.

In the process according to the invention, the compound S is added in the first distillation stage (4.1). This is preferably done by metering in the compound S in the form of a dilute, preferably three percent, more preferably two percent and especially one percent, solution in the particular target ester at the top of the column used for the low boiler removal (4.1). In addition, the mixture to be separated (3.2) may already comprise the compound S.

Accordingly, the bottom product (4.1.2) of the process according to the invention comprises not only the target ester and (meth)acrylic acid but also the compound S. The concentration of the compound S in the bottom product (4.1.2) may vary widely and is guided by the requirements of the individual case. Preference is given to metering in sufficient compound S that the bottom product (4.1.2) comprises from 10 to 10 000 ppm, preferably from 100 to 5000 ppm and especially from 100 to 1000 ppm of the compound S.

In the process according to the invention, the compound S is also added to the second distillation stage (4.2). This is preferably done by supplying the compound S in the form of a dilute, preferably three percent, more preferably two percent and especially one percent, solution in the particular target ester to the lower part of the column used for the purifying distillation (4.2).

Accordingly, the bottom product (4.2.2) of the process according to the invention comprises not only the target ester and (meth)acrylic acid but also the compound S. The concentration of the compound S in the bottom product (4.2.2) may vary widely and is guided by the requirements of the individual case. Preference is given to metering in sufficient compound S that the bottom product (4.2.2) comprises from 100 to 10 000 ppm, preferably from 200 to 5000 ppm and especially from 400 to 1000 ppm of the compound S.

The bottom product (4.2.2) of the process according to the invention is preferably recycled completely into the reactor. There, the compound S brings about additional stabilization before it is degraded by the catalyst.

For additional stabilization, hydroquinone monomethyl ether may also be metered into the reflux of the distillation column, so as to result in a concentration of from 10 to 500 ppm, especially from 20 to 150 ppm, of hydroquinone monomethyl ether in the bottom product (4.2.2).

The distillate (4.2.1) of the purifying distillation (4.2) consists of target ester of a particularly high purity. The purity is preferably >99.5% by weight, preferentially >99.8% by weight and especially >99.9% by weight. Since there is only a very low level of redissociation of the target esters and a very low level of polymerization in the removal of the target ester in process step (4)—if any—the yields are particularly high. Especially owing to the very low level of polymerization in the plant parts, the run times of the plants are particularly long.

Example

The preparation of tert-butyl acrylate (TBA) using 4-hydroxy-2,2,6,6-tetramethyl-1-oxylpiperidine (OH-Tempo)

In a customary and known reactor with feed lines for isobutene, sulfuric acid, phenothiazine (four percent in TBA) and acrylic acid (fresh acrylic acid of a purity of 99.9%, stabilized with hydroquinone monomethyl ether and acrylic acid from the bottom of the purifying distillation, comprising OH-Tempo), a discharge for the resulting reaction mixture and an offgas line, isobutene was reacted with an excess of acrylic acid (50 mol %). The resulting reaction mixture, which comprised TBA, acrylic acid, PTZ, hydroquinone monomethyl ether and catalyst, was discharged. The catalyst was, as described in DE 100 36 958 A1, example 1, the paragraph [0057] spanning columns 9 and 10, removed from the discharged reaction mixture. The resulting distillate comprising TBA was cooled in a heat exchanger, admixed with a one percent solution of OH-Tempo in TBA and fed to a distillation unit which consisted of an external circulation evaporator (natural circulation), a distillation column having 40 dual-flow trays (feed tray 22) and two condensers arranged in series. At the top of the column a one percent solution of OH-Tempo in TBA was likewise supplied in such an amount as to result in an overall concentration of OH-Tempo of 200 ppm in the bottom of the column. The low-boiling constituents (residual isobutene, diisobutene and tert-butanol) were removed, and the bottom product consisting essentially of acrylic acid, TBA and OH-Tempo was subjected to a purifying distillation in a further distillation unit. The distillation unit consisted of an external tube bundle evaporator, a distillation column having 40 dual-flow trays (feed tray 18) and two condensers arranged in series. A one percent solution of OH-Tempo in TBA was likewise fed to the middle part of the column in such an amount as to result in a concentration of OH-Tempo of from 400 to 700 ppm in the bottom of the column. The bottom product, which consisted essentially of acrylic acid, was recycled into the reactor. The TBA distilled off had a purity of 99.8%. The content of OH-Tempo was measured with the aid of electron spin resonance (ESR); however, no signal could be detected. The content was therefore below the detection limit of 0.3 ppm. After a run time of 60 d, the production was ended but only because no further storage tanks were available. Since no fouling had occurred in the column bottoms and no deposits of polymers on the column trays had occurred after this time, the continuous production could undoubtedly have been continued without any problem.

The invention claimed is:

1. A process for preparing tertiary alkyl esters of (meth) acrylic acid having at least 4 carbon atoms in the alkyl radical, comprising:
   (1) reacting (meth)acrylic acid with at least one olefin of formula I:

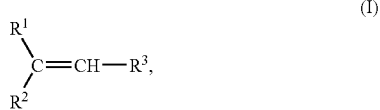

in which $R^1$ and $R^2$ may be the same or different and are each an alkyl radical, and $R^3$ is a hydrogen atom, an alkyl radical, a cycloalkyl radical, an aryl radical, an alkylcycloalkyl radical which is bonded to the olefinically unsaturated carbon atom via an aliphatic or cycloaliphatic carbon atom, an alkylaryl radical which is bonded to the olefinically unsaturated carbon atom via an aliphatic or aromatic carbon atom, a cycloalkylaryl radical which is bonded to the olefinically unsaturated carbon atom via a cycloaliphatic or aromatic carbon atom, or an alkylcycloalkylaryl radical which is bonded to the olefinically unsaturated carbon atom via an aliphatic, cycloaliphatic or aromatic carbon atom;
   in homogeneous phase in the presence of an acidic catalyst in a reactor to form a first mixture,
   (2) discharging said first mixture from the reactor to obtain a discharged reaction mixture,
   (3) separating the discharged reaction mixture into a catalyst mixture which comprises the catalyst and a tertiary alkyl ester mixture which comprises the tertiary alkyl ester of (meth)acrylic acid having at least 4 carbon atoms in the alkyl radical, and
   (4) removing the tertiary alkyl ester of (meth)acrylic acid having at least 4 carbon atoms in the alkyl radical from the tertiary alkyl ester mixture, which comprises,
   (5) in (4), adding in an amount of from 400 to 700 ppm, by weight, at least one compound S which comprises at least one N-oxyl group, as stabilizer.

2. The process according to claim 1, wherein the nitrogen atom of the N-oxyl group is part of a heterocyclic ring.

3. The process according to claim 2, wherein the heterocyclic ring is aliphatic.

4. The process according to claim 3, wherein the heterocyclic aliphatic ring is derived from a piperidine ring.

5. The process according to claim 1, wherein the N-oxyl group is sterically hindered.

6. The process according to claim 5, wherein the carbon atoms in the alpha positions to the nitrogen atom of the N-oxyl group each bear at least one alkyl group.

7. The process according to claim 6, wherein the carbon atoms in the alpha positions to the nitrogen atom of the N-oxyl group each bear 2 alkyl groups.

8. The process according to claim 6, wherein at least one of the 2 alkyl groups a methyl group.

9. The process according to claim 8, wherein the compound S comprises at least one 2,2,6,6-tetramethyl-1-oxylpiperidin-4-yl group.

10. The process according to claim 9, wherein the compound S is 4-hydroxy-2,2,6,6-tetramethyl-1-oxylpiperidine.

11. The process according to claim 1, wherein the catalyst mixture is recycled partly or fully into the reactor.

12. The process according to claim 1, wherein the tertiary alkyl ester mixture is removed as a distillate.

13. The process according to claim 1, wherein the tertiary alkyl ester of (meth)acrylic acid having at least 4 carbon atoms in the alkyl radical is removed from the tertiary alkyl ester mixture by two-stage distillation in (4), wherein said two-stage distillation comprises a first distillation stage and a second distillation stage.

14. The process according to claim 13, wherein the compound S is added in the first distillation stage and the second distillation stage.

15. The process according to claim 14, wherein the compound S is added to the tertiary alkyl ester mixture before the first distillation stage.

16. The process according to claim 14, wherein the tertiary alkyl ester mixture is separated in the first distillation stage into a low-boiling distillate and a first bottom product comprising the tertiary alkyl ester of (meth)acrylic acid having at least 4 carbon atoms in the alkyl radical and the compound S.

17. The process according to claim 16, wherein the first bottom product is separated in the second distillation stage into a tertiary alkyl ester distillate which consists essentially of the tertiary alkyl ester of (meth)acrylic acid having at least 4 carbon atoms in the alkyl radical and a second bottom product which comprises the compound S.

18. The process according to claim 17, wherein the second bottom product is recycled partly or fully into the reactor.

19. The process according to claim 1, wherein the olefin of the general formula I is isobutene.

20. The process according to claim 1, wherein Compound S is the only stabilizer present.

* * * * *